United States Patent [19]

Golub et al.

[11] Patent Number: 5,532,227
[45] Date of Patent: Jul. 2, 1996

[54] TETRACYCLINES INCLUDING NON-ANTIMICROBIAL CHEMICALLY-MODIFIED TETRACYCLINES INHIBIT EXCESSIVE GLYCOSYLATION OF DIFFERENT TYPES OF COLLAGEN AND OTHER PROTEINS DURING DIABETES

[75] Inventors: Lorne M. Golub; Nungavarum S. Ramamurthy, both of Smithtown; Thomas F. McNamara, Port Jefferson; Maria E. Ryan, Port Jefferson Station, all of N.Y.

[73] Assignee: The Research Foundation of State University of New York, Albany, N.Y.

[21] Appl. No.: 361,116

[22] Filed: Dec. 21, 1994

Related U.S. Application Data

[63] Continuation-in-part of Ser. No. 977,549, Nov. 17, 1992, abandoned.

[51] Int. Cl.$^6$ ............................................... A61K 31/65
[52] U.S. Cl. ............................ 514/152; 514/866; 514/912
[58] Field of Search ............................... 514/152, 866, 514/912

[56] References Cited

U.S. PATENT DOCUMENTS

| 4,935,412 | 6/1990 | McNamara et al. | 514/152 |
| 5,045,538 | 9/1991 | Schneider et al. | 514/152 |
| 5,258,371 | 11/1993 | Golub et al. | 514/152 |

*Primary Examiner*—John W. Rollins
*Attorney, Agent, or Firm*—Hoffmann & Baron

[57] ABSTRACT

A method for treating mammals suffering from excessive extracellular protein glycosylation which is associated with diabetes, scleroderma and progeria by administering to the mammal a tetracycline which effectively inhibits excessive protein glycosylation.

11 Claims, 9 Drawing Sheets

FIG-1 BLOOD GLUCOSE LEVEL

FIG-4 TETRACYCLINE Tx REDUCES PROTEINURIA: EFFECT ON VOLUME AND PROTEINURIA

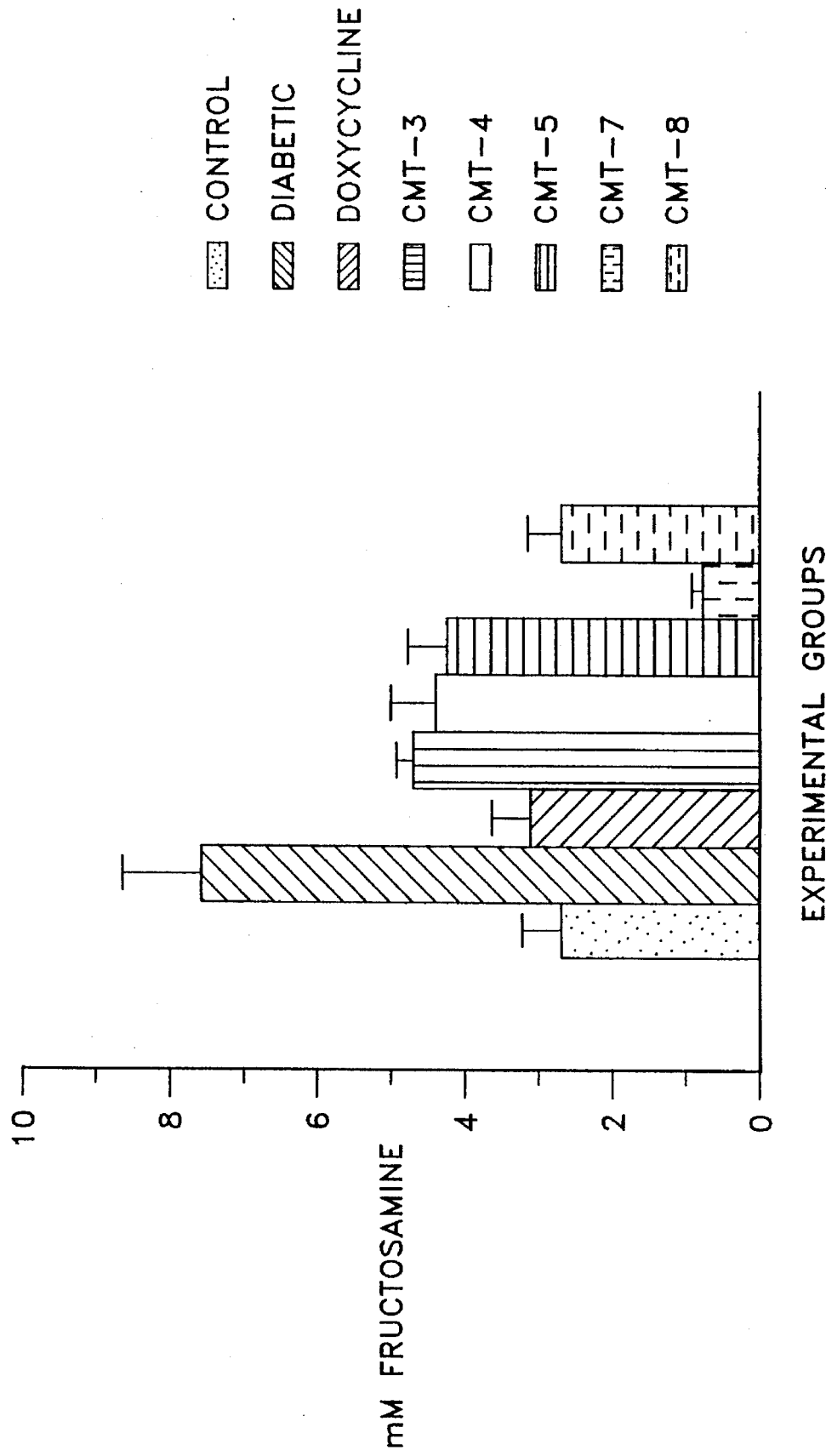
FIG-7 THE EFFECT OF DIABETES AND CMT THERAPY ON GLYCOSYLATED SERUM PROTEIN LEVELS

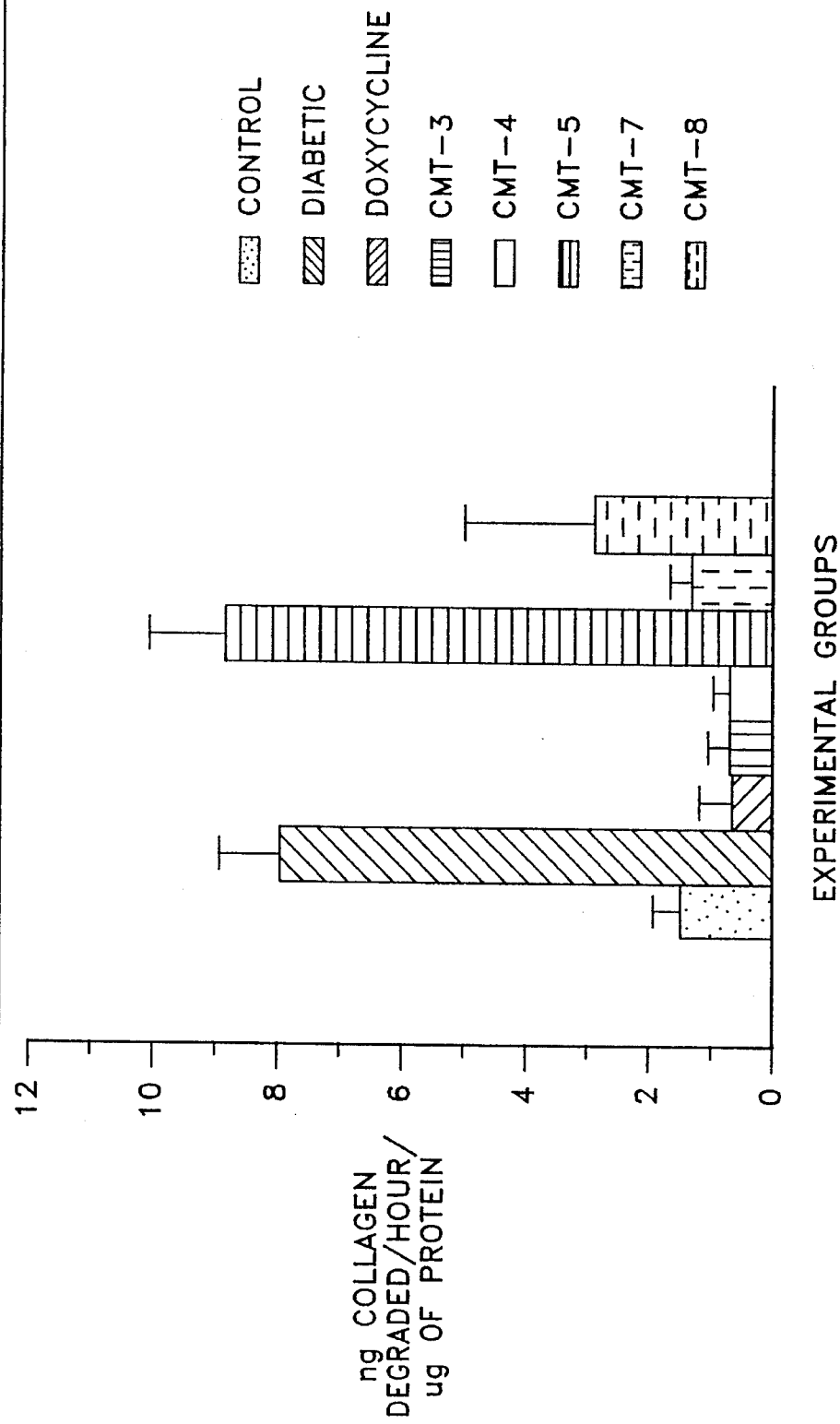
FIG-8 COLLAGENASE ACTIVITY IN THE SKIN OF DIABETIC RATS: EFFECT OF CMT THERAPY

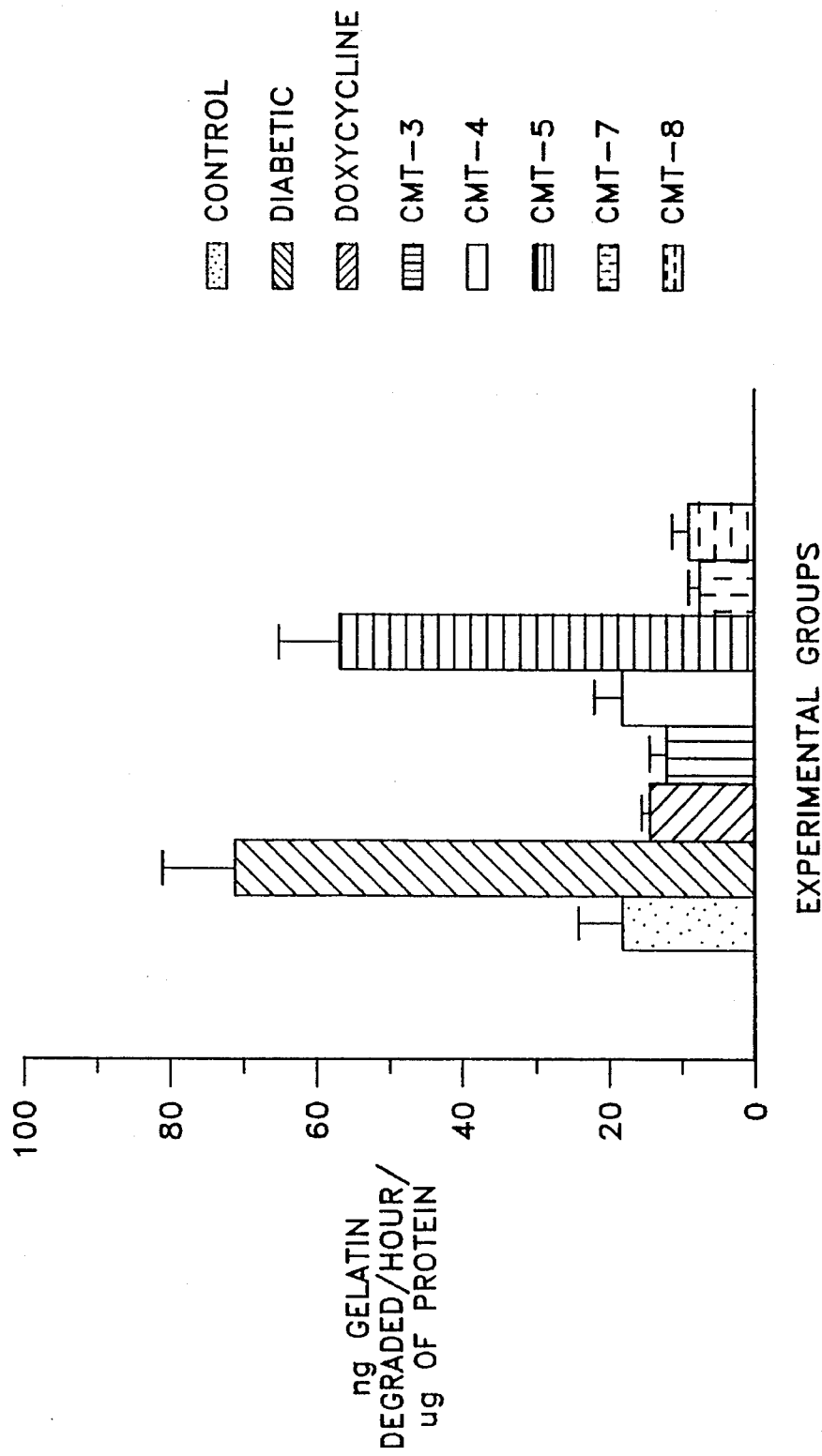

TETRACYCLINES INCLUDING NON-ANTIMICROBIAL CHEMICALLY-MODIFIED TETRACYCLINES INHIBIT EXCESSIVE GLYCOSYLATION OF DIFFERENT TYPES OF COLLAGEN AND OTHER PROTEINS DURING DIABETES

This invention was made with Government support under R37 DE-03987, awarded by The National Institute of Dental Research. The Government has certain rights in the invention.

BACKGROUND OF THE INVENTION

The present application is a continuation-in-part of U.S. patent application Ser. No. 07/977,549 filed on Nov. 17, 1992, now abandoned.

The present invention relates to a method of treating mammals suffering from conditions associated with an excessive amount of protein glycosylation, by administering to the mammal an amount and/or type of a tetracycline that is not effectively antimicrobial but which effectively inhibits excessive protein glycosylation. All somatic proteins with exposed amino groups are subject to extracellular non-enzymatic glycosylation. Several proteins including collagens (e.g., Type I and Type IV collagen), lens crystallins, laminin, albumin, fibrin and low-density lipoproteins are known to be glycosylated in various disease states. For example, excessive glycosylation of the diabetic basement membrane contributes to the complication of kidney disease or nephropathy.

In diabetes mellitus excessive glycosylation of collagen results in an excessive amount of collagen crosslinking. This pathological complication of excessive collagen glycosylation and the resulting excessive collagen crosslinking during diabetes mellitus is discussed in detail below. Other conditions associated with an excessive amount of collagen glycosylation and resulting collagen crosslinking include scleroderma and progeria.

Diabetes mellitus (diabetes) is a complex disease that affects several hundred million people world wide. Diabetes is characterized by an elevated level of glucose in the blood. Glucose cannot enter the body's cells to be utilized and therefore remains in the blood in high concentrations. When the blood glucose level exceeds the reabsorptive capacity of the renal tubules, glucose is excreted in the urine. Diabetes produces a number of debilitating and life-threatening complications.

A number of diabetes-induced abnormalities in collagen metabolism, such as pathologically-excessive collagenase activity in gingiva and skin, have been reported in the literature. Ramamurthy et al., *J. Peridontal Res.* 17: 455–462 (1983); Golub et al, *J. Peridontal Res.* 18: 516–526 (1983). Ramamurthy et al., *Gerondontol.* 2(1): 15–19 (1983). A complication of excessive collagenase activity is an unusually aggressive periodontal destruction which is frequently associated with diabetes. Golub et al, *J. Peridontal Res.* 18: 516–526 (1983). This complication is particularly problematic when the disease is poorly controlled. Ainamo et al., *J. Clin. Peridontol.* 17: 22–28 (1990); Finestone et al., *Diabetes* 16: 336–340 (1967).

Intracellular collagen biosynthesis is a complex process characterized by extensive posttranslational modifications. Jackson, The Substrate Collagen, Chapter 1, in: "Collagenase In Normal And Pathological Connective Tissues," (eds: D. E. Woolley and J. M. Evanson), pp 1–10, John Wiley & Sons Ltd., New York, 1980. After secretion into the extracellular matrix, collagen crosslinking results from two different biochemical pathways, enzymatic lysyl oxidase-dependent oxidative deamination and nonenzymatic glucose-derived glycosylation. Buckingham et al., *J. Clin. Invest.* 86:1046 (1990).

Intracellular events include the hydroxylation of certain lysine and proline residues and enzymatically mediated glycosylation of hydroxylysine before the pro-collagen (collagen precursor) molecule is secreted from the cell. C-terminal and N-terminal extension peptides are subsequently cleaved. Extracellularly, the collagen molecules become stabilized in their fibrillar arrays or networks by covalent cross-linking mediated initially by the enzyme, lysyl oxidase. Nonenzymatic glycosylation of certain lysine and hydroxylysine residues also occurs in the extracellular matrix. This modification appears to have direct effects on collagen structure and function as well as indirect effects which arise as a result of further reactions of the glycosylated residues.

A "hallmark" abnormality in collagen metabolism in the connective tissues of the diabetic is a reduction in the extractability or solubility of collagen in either cold (0–4° C.) neutral salt or dilute acid solutions. This reduction in collagen solubility reflects excessive inter,- and intramolecular covalent crosslinking of the collagen molecules. Diabetes-induced reduction in collagen solubility, due to excessive collagen crosslinking, has been seen in a variety of tissues including (but not limited to) skin, bone, tendon, gingiva, aorta and dura matter. Ramamurthy et al., *Gerondontology* 2: 15 (1983); Brownlee et al., *Science* 232:1629 (1986); Buckingham et al., *J. Clin. Invest.* 86:1046 (1990); Dominiczak et al., *Diabetes Care* 13:468 (1990); Golub et al., *Biochim. Biophys. Acta* 534:73 (1978). Abnormally low solubility of collagen reflects the excessive crosslinking of collagen in the extracellular matrix which renders the collagen excessively polymerized and more resistant to degradation and turnover. (See Golub et al., *BioShim. Biophys. Acta* 534:73 (1978), for a review).

Hamlin et al., (*Diabetes* 24:902 (1975)) and others describe this reduced collagen solubility/increased collagen crosslinking, which characterizes the connective tissues of the diabetic, as an "aging-like" abnormality in collagen metabolism. This abnormality is increasingly viewed as a major cause of numerous complications of diabetes including (but not limited to) increased leatheriness of skin, limitation of joint movement, increased stiffness of arterial walls, impaired wound healing, decreased elasticity of lungs, nephropathy including proteinuria, and retinopathy.

Recent studies (Walton et al., *Biochim. Biophys. Acta,* 1138:172–183 (1992)) have demonstrated that crosslinking of basement membranes (type IV collagen) of the kidney glomerulus increases the permeability of the basement membrane to protein which, in turn, promotes proteinuria, a classic parameter of renal damage in the diabetic. As discussed earlier, diabetes mellitus results in increased crosslinking of collagens. Cohen et al., (*Biochem. Biophys. Res. Commun.,* 95:765–769 (1980)) have found that inducing diabetes in rats increases nonenzymatic glycosylation of glomerular basement membranes. As previously mentioned, non-enzymatic glycosylation provides one mechanism for excessive collagen crosslinking. Reiser, *Proc. Soc. Experiment. Biol. and Med.,* 196:17–29 (1991).

Abnormally excessive, or increased collagen crosslinking during diabetes is mediated by both mechanisms described above. It is mediated enzymatically by the excessive activity of lysyl oxidase and non-enzymatically by the glucose-derived mechanism due to exposure to elevated blood and tissue fluid glucose concentrations which characterizes the uncontrolled diabetic state. Makita et al., *New Engl. J. Med.* 325:836 (1991); Cerami et al., *Diabetes Care* (Suppl.1:73) (1988).

Enzymatic lysyl oxidase-dependent collagen crosslinking begins with lysyl oxidase-dependent oxidative deamination of certain lysine and hydroxylysine residues. The resultant aldehyde moilties may undergo further reactions with lysine, hydroxylysine, and histidine residues to form di-, tri- and tetrafunctional crosslinks. Robbins, *Methods Biochem. Analysis* 28: 330–379 (1982). In particular, lysyl oxidase converts ε-amino groups of certain lysyl and hydroxylysyl residues, in the non-helical regions of the collagen molecule, to aldehyde moieties which then form Schiff base crosslinks with adjacent molecules. Vader, et al., *Biochem. J.* 180: 639–645 (1979).

As previously mentioned, nonenzymatic glucose-derived crosslinking begins with the nonenzymatic glycosylation of the ε-amino groups of lysine and hydroxylysine residues on the collagen molecules in the extracellular matrix. These early glycosylation products are believed to undergo a series of reactions to form complex fluorophores and chromophores collectively referred to as advanced Maillard products or advanced glycosylation end-products ("AGES"). Brownlee et al., *N. Engl. J. Med.* 318: 1315–1322 (1988).

Brownlee et al., (*Science* 232: 1629–1632 (1986)) have reported that aminoguanidine is an effective inhibitor of nonenzymatic glucose-derived collagen crosslinking associated with diabetes in rats and, as a result reduces the severity of some diabetic complications. However, aminoguanidine has not been approved for use in humans. Various tetracyclines, on the other hand, have been approved for use in humans.

The compound, tetracycline, exhibits the following general structure:

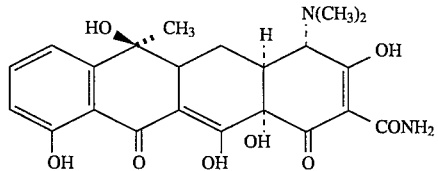

The numbering system of the ring nucleus is as follows:

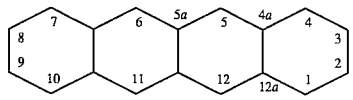

Tetracycline as well as the 5-OH (Terramycin) and 7-Cl (Aureomycin) derivatives exist in nature, and are well known antibiotics. Natural tetracyclines may be modified without losing their antibiotic properties, although certain elements of the structure must be retained. The modifications that may and may not be made to the basic tetracycline structure have been reviewed by Mitscher in *The Chemistry of Tetracyclines*, Chapter 6, Marcel Dekker, Publishers, New York (1978). According to Mitscher, the substituents at positions 5–9 of the tetracycline ring system may be modified without the complete loss of antibiotic properties. Changes to the basic ring system or replacement of the substituents at positions 1–4 and 10–12, however, generally lead to synthetic tetracyclines with substantially less or effectively no antimicrobial activity. For example, 4-dedimethylaminotetracycline is commonly considered to be a non-antimicrobial tetracycline.

The use of tetracycline antibiotics, while effective, may lead to undesirable side effects. For example, the long-term administration of antibiotic tetracyclines may reduce or eliminate healthy flora, such as intestinal flora, and may lead to the production of antibiotic resistant organisms or the overgrowth of opportunistic yeast and fungi. These side-effects of long-term tetracycline therapy can be particularly disadvantageous to patients with diabetes because these patients are particularly susceptible to infection and impaired wound healing which might, at some future time, require antibiotic therapy to combat infection.

In addition to their antibiotic properties, tetracyclines have been described for a number of uses. For example, tetracyclines are also known to inhibit the activity of collagen destructive enzymes such as mammalian collagenase, gelatinase, macrophage elastase and bacterial collagenase. Golub et al., *J. Periodont. Res.* 20: 12–23 (1985); Golub et al. *Crit. Revs. Oral Biol. Med.* 2: 297–322 (1991).

Tetracyclines, administered at both antimicrobial levels and non-antimicrobial levels, have been known to play a role in reducing collagenase and other collagenolytic enzyme activity as well as collagen breakdown, U.S. Pat. Nos. 4,666,897; 4,704,383; 4,935,411; 4,935,412. This anticollagenase activity of tetracyclines, which protects collagen from proteinase attack, can also protect the serum protein, $\alpha_1$ proteinase inhibitor ($\alpha_1$-PI) from proteolytic degradation/inactivation as well. Sorsa et al., (1993) *Antimicrobial Agents & Chemo.*, 37: 592. $\alpha_1$-PI is the body's major defense against other tissue-destructive proteinases, (i.e., serine-proteinases, such as elastase and cathepsin G). In addition, tetracyclines have been known to inhibit wasting and protein degradation in mammalian skeletal muscle, U.S. Pat. No. 5,045,538. Furthermore, tetracyclines have been demonstrated to enhance bone protein synthesis, U.S. Pat. No. Re. 34,656.

U.S. Pat. No. 4,704,383 to McNamara et al. discloses that tetracyclines having substantially no effective antimicrobial activity inhibit collagenolytic enzyme activity in rats. McNamara et al. also report that non-antimicrobial tetracyclines reduce bone resorption in organ culture. Earlier, U.S. Pat. No. 4,666,897 to Golub, et al. disclosed that tetracyclines in general, including commercially-available antimicrobial forms of the drug, inhibit excessive mammalian collagenolytic enzyme activity resulting in decreased connective tissue breakdown including that which occurs during bone resorption.

There have been a number of suggestions that tetracyclines, including non-antimicrobial tetracyclines, are effective in treating arthritis in rats. See, for example, Golub et al, "Tetracyclines (TCs) Inhibit Matrix Metalloproteinases (MMPs): In Vivo Effects in Arthritic and Diabetic Rats And New In Vitro Studies," *Matrix*, Suppl. No. 1:315–316 (1992); Greenwald et al. "CMT, A Matrix Metalloproteinase Inhibitor, Prevents Bone Resorption In Adjuvant Arthritis." *Arthritis Rheum.:* 34 (#9 suppl): S66 (abstract #A6), abstract presented at 55th Annual Meeting, Amer. College of Rheumatology, Boston, Mass., Nov. 18, 1991; Breedveld, "Suppression of Collagen And Adjuvant Arthritis By A Tetracycline," Northeastern Regional Meeting Of The Amer. Rheum. Assoc., Atlantic City, N.J., Oct. 23, 1987. For a related commentary regarding the effect of non-antimicrobial tetracyclines on bone loss see Sipos et al., "The Effect of Collagenase Inhibitors On Alveolar Bone Loss Due To Periodontal Disease In Desalivated Rats," abstract presented at Matrix Metalloproteinase Conference, Destin, Fl., Sep. 11–15, 1989.

According to White, *Lancet*, Apr. 29, p. 966 (1989) the tetracycline minocycline is effective in treating dystrophic epidermolysis bullosa, which is a life-threatening skin condition believed to be related to excess collagenase.

The effectiveness of tetracycline in skin disorders has also been studied by Elewski et al., *Journal of the American Academy of Dermatology* : 807–812 (1983). Elewski et al. disclosed that tetracycline antibiotics may have anti-inflammatory activity in skin and speculate that a portion of the therapeutic effect in skin diseases associated with bacteria, e.g., acne, may be due to inhibition of bacterially induced inflammation rather than a direct antimicrobial effect.

Similarly, Plewig et al., *Journal of Investigative Dermatology* 65: 352 (1975), disclose experiments designed to test the hypothesis that antimicrobials are effective in treating inflammatory dermatoses. The experiments of Plewig et al. establish that tetracyclines have anti-inflammatory properties in treating pustules induced by potassium iodide patches.

The use of tetracyclines in combination with non-steroidal anti-inflammatory agents has been studied in the treatment of inflammatory skin disorders caused by acne vulgaris. Wong et al., *Journal of American Academy of Dermatology* 11: 1076–1081 (1984), studied the combination of tetracycline and ibuprofen and found that tetracycline was an effective agent against acne vulgaris while ibuprofen was useful in reducing the resulting inflammation by inhibition of cyclooxygenase. Funt, *Journal of the American Academy of Dermatology* 13: 524–525 (1985), disclosed similar results by combining antimicrobial doses of minocycline and ibuprofen.

Based on the foregoing, tetracyclines have been found to be effective in different treatments. However, there has been no suggestion whatsoever that tetracyclines can ameliorate the excessive glycosylation of proteins. In particular, tetracyclines have been found to inhibit the excessive glycosylation of collagen. Consequently, tetracyclines inhibit the excessive collagen crosslinking which results from excessive glycosylation of collagen. In addition, a number of tetracyclines have been found to have no significant effect on reduction of the severity of hyperglycemia associated with diabetes. Golub et al., *J. Periodontal Res.*, 18: 516–526 (1983); Golub et al., *Res. Commun. Chem. Path. Pharmacol.*, 68:27–40 (1990); Yu et al., *J. Periodontal Res.*, 28: 420–428 (1993).

On the other hand, insulin, unlike tetracycline, is useful in the treatment of diabetes, including reducing the severity of hyperglycemia. However, most insulin-treated diabetics still exhibit some degree of hyperglycemia which can ultimately lead to excessive glycosylation of collagen. It is not clear which mechanism, enzymatic lysyl oxidase-dependent oxidative deamination or nonenzymatic glucose-derived collagen glycosylation, is predominantly responsible for the excessive collagen crosslinking resulting from hyperglycemia and diabetes mellitus.

The present invention is intended to provide a means for treating excessive glycosylation of proteins. The present invention demonstrates that tetracyclines, including their chemically-modified analogs which have lost their antimicrobial efficacy, and even those chemically-modified tetracycline analogs that have lost their anticollagenase activity, have a novel new use, the ability to inhibit excessive protein glycosylation. This non-antimicrobial and non-anticollagenase property of tetracyclines reduces the severe complications of many diseases. In the case of diabetes, this includes the amelioration of proteinuria which is a sign of diabetes-induced nephropathy (a life-threatening complication of the disease).

SUMMARY OF THE INVENTION

The present invention provides a method for treating mammals suffering from excessive protein glycosylation which is associated with diseases such as (but not limited to) diabetes, scleroderma and progeria. The method of the present invention includes administering to the mammal an amount and/or type of a tetracycline which effectively inhibits excessive protein glycosylation. All body proteins with exposed amino groups are subject to a pathologically excessive amount of glycosylation. Examples of these proteins include collagens, albumin, fibrin, lens crystallins and laminin. A pathologically excessive amount of collagen glycosylation results in a pathologically excessive amount of collagen crosslinking. Pathologically excessive collagen crosslinking is associated with disease conditions including diabetes mellitus, scleroderma and progeria.

Chemically-modified tetracyclines, for example dedimethylaminotetracyclines, are useful in the present invention. Dedimethylaminotetracyclines include 4-dedimethylaminotetracycline, 4-dedimethylamino-5-oxytetracycline, 4-dedimethylamino-7-chlorotetracycline, 4-hydroxy-4-dedimethylaminotetracycline, 5a, 6-anhydro-4hydroxy-4-dedimethylaminotetracycline, 6α-deoxy-5-hydroxy-4-dedimethylaminotetracycline, 6-demethyl-6-deoxy-4-dedimethylaminotetracycline, 4-dedimethylamino-12a-deoxytetracycline, 4-dedimethylamino-11-hydroxy-12a-deoxytetracycline, 12a-deoxy-4-deoxy-4-dedimethylaminotetracycline, 6α-deoxy-5-hydroxy-4-dedimethylaminodoxycycline, 12a,4a-anhydro-4-dedimethylaminotetracycline and minocycline-CMT i.e., 7-dimethylamino-6-demethyl-6-deoxy-4-dedimethylaminotetracycline.

Further examples of chemically-modified tetracyclines useful in the present invention are 6a-benzylthiomethylenetetracycline, the 2-nitrilo analogs of tetracycline (tetracyclinonitrile), the mono-N-alkylated amide of tetracycline, 6-fluoro-6-demethyltetracycline, 11a-chlorotetracycline, tetracycline pyrazole and 12a-deoxytetracycline and its derivatives.

The non-antimicrobial tetracycline is administered in an amount of from about 0.1 mg/kg per day to about 50.0 mg/kg per day, preferably from about 0.3 mg/kg per day to about 15.0 mg/kg per day.

The method of the present invention ameliorates many of the complications associated with diabetes, for example, increased leatheriness of skin, decreased lung elasticity, increased arterial wall stiffness, limitation of joint movement, impaired wound healing, nephropathy resulting in proteinuria, and retinopathy.

For a better understanding of the present invention, reference is made to the following description, taken together with the accompanying drawings, and its scope will be pointed out in the appended claims.

BRIEF DESCRIPTION OF THE DRAWINGS

All tetracyclines in FIGS. 1–9 were orally administered daily unless otherwise indicated.

FIG. 7 is a graphic representation of the effect of doxycycline, CMT-3 (6-demethyl-6-deoxy-4-dedimethylaminotetracycline), CMT-4 (7-chloro-4-dedimethylaminotetracycline), CMT-5 (tetracycline pyrazole), CMT-7 (12a-deoxy -4-deoxy-4-dedimethylaminotetracycline), and CMT-8 (6α-deoxy-5-hydroxy-4-dedimethylaminodoxycycline) on glycosylated serum proteins (GSP) in streptozotocin-diabetic rats.

FIG. 8 is a graphic representation of the effect of doxycycline, CMT-3 (6-demethyl-6-deoxy-4-dedimethylaminotetracycline), CMT-4 (7-chloro-4-dedimethylaminotetracycline), CMT-5 (tetracycline pyrazole), CMT-7 (12a-deoxy -4-deoxy-4-dedimethylaminotetracycline), and CMT-8 (6α-deoxy-5-hydroxy-4-dedimethylaminodoxycycline) on collagenase activity in the skin of streptozotocin-diabetic rats.

FIG. 9 is a graphic representation of the effect of doxycycline, CMT-3 (6-demethyl-6-deoxy-4-dedimethylaminotetracycline), CMT-4 (7-chloro-4-dedimethylaminotetracycline), CMT-5 (tetracycline pyrazole), CMT-7 (12a-deoxy -4-deoxy-4-dedimethylaminotetracycline), and CMT-8 (6α-deoxy-5-hydroxy-4-dedimethylaminodoxycycline) on gelatinase activity in the skin of streptozotocin-diabetic rats.

DETAILED DESCRIPTION OF THE INVENTION

Figure 1:
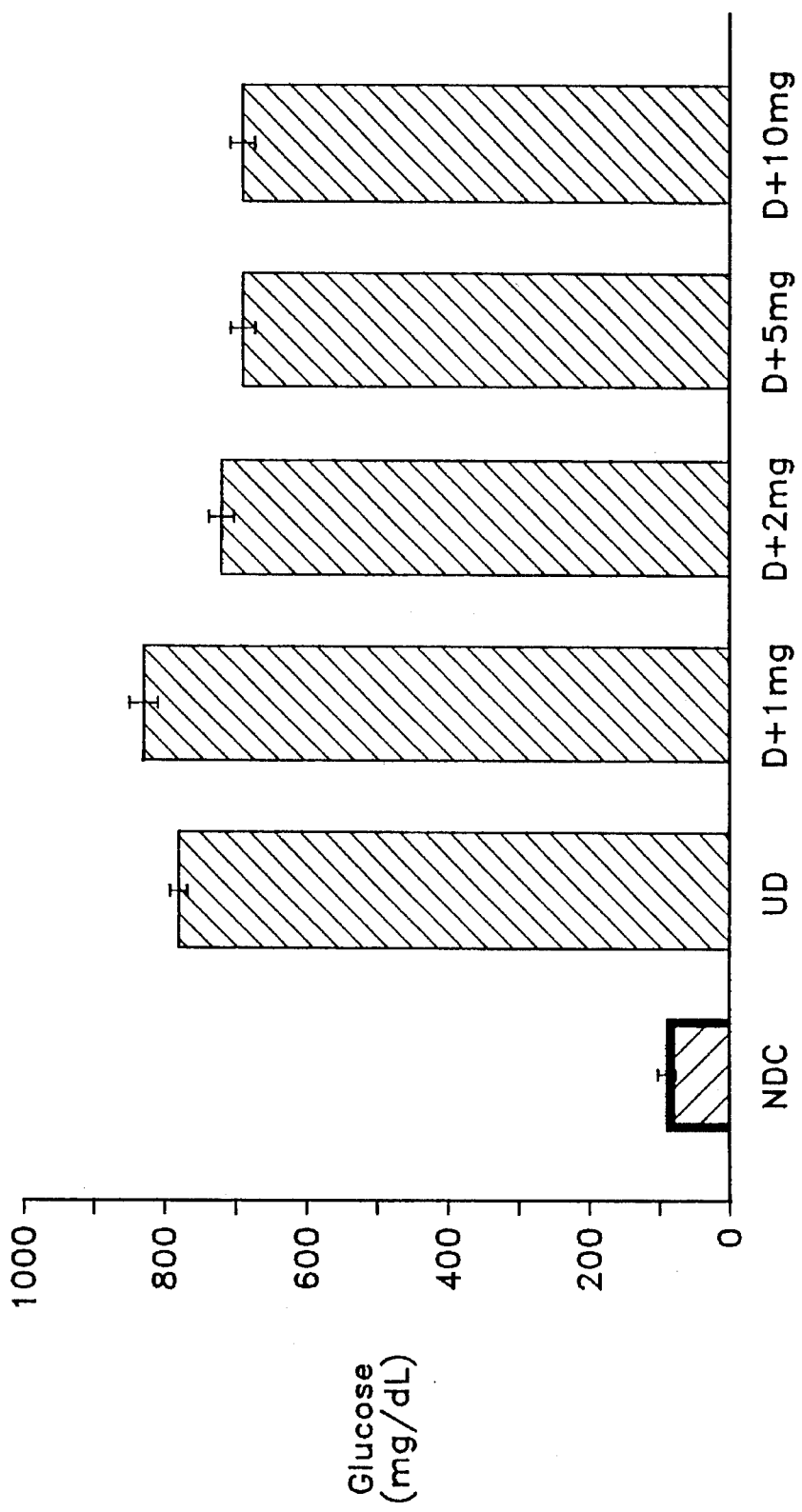
FIG. 1 is a graphic representation of the effect of different oral doses of CMT-1 (4-dedimethylaminotetracycline) on the blood glucose concentration (mg/dL) of streptozotocin-diabetic rats. Each value represents the mean ± S.E.M. for 4 rats per experimental group.

It has been discovered that tetracyclines inhibit the excessive glycosylation of proteins and, in particular excessive collagen glycosylation. Excessive collagen glycosylation results in excessive collagen crosslinking associated with diabetes, scleroderma and progeria. In particular, it has been discovered that the use of certain tetracyclines inhibits excessive collagen glycosylation. Various tetracyclines have been shown not to affect blood glucose levels in diabetic rats. The tetracyclines of the present invention have clearly demonstrated an ability to inhibit glycosylation of collagen and other proteins. The tetracyclines of the present invention can be combined with insulin therapies, which are known to moderate blood glucose levels in the treatment of diabetes. While the tetracycline inhibits excessive collagenglycosylation, the insulin attempts to regulate hyperglycemia. As previously mentioned, the diabetic complications associated with excessive collagen glycosylation and the resulting collagen crosslinking include increased leatheriness of skin, decreased lung elasticity, increased arterial wall stiffness, limitation of joint movement, impaired wound healing and nephropathy resulting in proteinuria, and retinopathy which can lead to blindness.

The excessive collagen crosslinking inhibitory effect is associated with the unexpected ability of tetracyclines to reduce glycosylation of protein. While not wishing to be bound by any one theory, it is believed that this inhibitory effect on pathologically-excessive collagen crosslinking is associated with the unexpected ability of tetracyclines to reduce nonenzymatic glucose-derived collagen glycosylation.

The conditions treated by the present invention occur in mammals. Mammals include, for example, human beings and laboratory animals such as mice and rats.

The tetracyclines useful in the present invention may be any tetracycline administered to a mammal in a dose that is preferably, effectively non-antimicrobial in the mammal. Preferably, the tetracycline is modified so as to reduce its antimicrobial properties. Methods for reducing the antimicrobial properties of a tetracycline are disclosed in "The Chemistry of the Tetracyclines", Chapter 6, Mitscher, Marcel Dekker, Publishers, New York (1978), at page 211. As pointed out by Mitscher, modifications at positions 1, 2, 3, 4, 10 and 12a lead to loss of antimicrobial bioactivity. Non-antimicrobial tetracyclines are preferred since they can be used at therapeutic levels which impart fewer side effects than antimicrobial tetracyclines at the same dosage level.

The preferred tetracyclines are those that lack the dimethylamino group at position 4. Such chemically modified tetracyclines include, for example, 4-dedimethylaminotetracycline, 4-dedimethylamino-5oxytetracycline, 4-dedimethylamino-7-chlorotetracycline, 4-hydroxy-4-dedimethylaminotetracycline,5a, 6-anhydro- 4-hydroxy-4-dedimethylaminotetracycline, 6-demethyl-6-deoxy-4-dedimethylaminotetracycline, 6α-deoxy-5-hydroxy-4-dedimethylaminotetracycline, 4-dedimethylamino-11-hydroxy-12a-deoxytetracycline, 4-dedimethylamino-12a-deoxytetracycline, 12a-deoxy- 4-deoxy-4-dedimethylaminotetracycline, 6α-deoxy-5 -hydroxy-4-dedimethylaminodoxycycline, 12a,4a-anhydro-4-dedimethyaminotetracycline and minocycline-CMT i.e., 7 -dimethylamino-6-demethyl-6-deoxy-4-dedimethylamino -tetracycline. Tetracyclines altered at the 2 carbon position to produce a nitrile, e.g., tetracyclinonitrile, may be useful as non-antimicrobial agents exhibiting anti-collagen glycosylation properties when administered via non-oral routes.

Further examples of tetracyclines modified for reduced antimicrobial activity include 6a-benzylthiomethylenetetracycline, the mono-N-alkylated amide of tetracycline, 6-fluoro-6 -demethyltetracycline, 11a-chlorotetracycline, tetracycline pyrazole and 12a-deoxytetracycline and its derivatives.

The effective amount of tetracycline is that amount which effectively inhibits excessive collagen glycosylation while it is not effectively antimicrobial. For purposes of this invention, a tetracycline effectively inhibits excessive collagen glycosylation if it is present in an amount which significantly reduces excessive collagen glycosylation. Excessive collagen glycosylation is defined as collagen glycosylation which is greater than that found in connective tissues of a nondiabetic control or normal control of the same age. (See Hamlin et al., *Diabetes* 24:902 (1975)).

A tetracycline is considered effectively non-antimicrobial if it does not significantly prevent the growth of microbes. This of course may vary depending upon a number of factors, such as, type of tetracycline, disease state and type of microbe. The maximal useful dosage for humans is the highest dosage that does not cause serious adverse side effects. For example, for purposes of the present invention, side effects include emergence of tetracycline—resistant microorganisms and overgrowth of opportunistic yeast and fungi, as well as toxic effects. A dose in excess of about 30 mg/kg/day would produce side effects in most mammals, including humans. The non-antimicrobial tetracycline of the present invention may be administered in an amount of from about 0.1 mg/kg/day to about 50.0 mg/kg/day preferably from about 0.3 mg/kg/day to about 15.0 mg/kg/day.

The means of delivery of the tetracycline with a pharmaceutically acceptable carrier may be in a variety of forms including capsules, compressed tablets, pills, solutions, suspensions, gels and creams. It is contemplated that carriers be included which are suitable for administration orally, topically, by injection and by other selected means.

EXAMPLES

The following examples serve to provide further appreciation of the invention but are not meant in any way to restrict the effective scope of the invention.

EXAMPLE I

Twenty-four adult male Sprague-Dawley rats were weighed (body weight between 350–375 g) and injected through the tail vein with either 0.9% saline (nondiabetic controls, NDC) or with the same solution containing streptozotocin (75 g streptozotocin/kg body weight) to induce diabetes. The diabetic rats were distributed into five experimental groups (n=4 rats per group) and daily administered by oral gavage either 0, 1, 2, 5 or 10 mg of CMT-1 (4-dedimethylaminotetracycline, a chemically-modified non-antimicrobial tetracycline) suspended in 2% carboxymethylcellulose (CMC) for 21 days. The non-diabetic control rats were gavaged with the carrier alone (2% CMC). Urine glucose levels were measured weekly with Tes-Tape (Eli Lily, Inc., Indianapolis, Ind.).

On the 21st day, the rats were weighed and anesthetized with halothane (Halocarbon Laboratories) before blood samples were collected for serum glucose (Sigma glucose oxidase kit, St. Louis, Mo.) and CMT-1 determinations. The rats were then killed by exsanguination and the skin from the entire torso was dissected, weighed, and minced as described by Schneir et al., *Diabetes* 31:426 (1982).

Skin samples were examined for collagen solubility using the techniques described previously (Golub et al., *J. Periodont. Res.* 12:402 (1977), Golub et al., *Biochim. Biophys. Acta* 534:73 (1978)) with some modifications. Except where indicated, all steps were carried out at 4° C.

Briefly, for the preparation of neutral salt-soluble collagen, minced rat skin was extracted with Tris-HCl buffer (pH 7.4) for 2 days followed by centrifugation at 11,000×g for 20 min. The pellet was subjected to an additional extraction for 18 hr and centrifuged as described above. Both supernatants were then combined and dialyzed exhaustively against 3% acetic acid for 2 days.

For the preparation of acid-soluble collagen, the pellet was further extracted with 3% acetic acid as described for the neutral salt extraction. The neutral salt and dilute acid extracts were dried with a rotatory evaporator at 60° C. under vacuum.

For the preparation of insoluble collagen, distilled water was added to the remaining pellet, which was heated at 121° C. for 15 min. under pressure and then vacuum dried as previously described. Following acid hydrolysis, the dried samples from the two extractions were used for neutral salt- and acid-soluble collagen determinations, while the pellet was used to determine the amount of insoluble collagen.

The amount of collagen in the three different skin fractions was also estimated. In particular, aliquots of the hydrolysates were repeatedly evaporated and reconstituted with distilled water to remove the hydrochloric acid. After removal of hydrochloric acid, the aliquots Were colorimetrically analyzed for hydroxyproline, an amino acid "marker" of collagen.

The extraction and HPLC determination of the concentration of CMT-1 in rat serum was carried out as described by Yu et al., *Biochem. Med. & Metabolic Biol.* 47:10–20 (1992).

The data were subject to statistical analysis. The standard error of the mean (S.E.M) was calculated from the standard deviation. The statistical significance between the groups were determined by analysis of variance while the significance of differences between groups was calculated by Tukey's test.

RESULTS

As seen in FIG. 1, three weeks after inducing diabetes with streptozotocin, the rats were severely hyperglycemic; the non-diabetic controls (NDC group) and the untreated diabetics (UD group) exhibited blood glucose levels of 95 mg/dL ± 3 (S.E.M.) and 787 mg/dL ± 10, respectively ($p < 0.01$). Treating the diabetic rats with the different oral doses of CMT-1, ranging from 1–10 mg/day, did not significantly alter the severity of hyperglycemia ($p < 0.05$).

Serum CMT-1 concentration was assayed using the HPLC technique described by Yu et al., *BioChem. Med. & Metabolic Biol.* 47: 10–20 (1992). The results demonstrate that increasing the dose of the drug, orally administered to the diabetic rats, increased the serum concentration for individual rats from 0.6 (for the 1 mg oral dose) to 6.5 µg/ml (for the 10 mg oral dose) (data not shown). Table I shows that the serum CMT-1 concentration for the different experimental groups was increased from a mean of 0.75 (for 1 mg oral dose) to 5.8 µg/ml (for the 10 mg oral dose).

TABLE I

The Oral Administration of Increasing Doses of CMT-1 to Streptozotocin-Diabetic Rats: Resulting Serum CMT-1 Concentrations ☉

| Experimental Groups | Serum CMT-1 Conc. (μg/ml) |
|---|---|
| NDC | 0 ± 0 |
| UD | 0 ± 0 |
| D + 1 mg CMT/day | 0.75 ± 0.04 |
| D + 2 mg CMT/day | 1.75 ± 0.05 |
| D + 5 mg CMT/day | 3.90 ± 0.16 |
| D + 10 mg CMT/day | 5.80 ± 0.25 |

☉ Each value represents the mean of 4 rats per group ± S.E.M.

Figure 2:
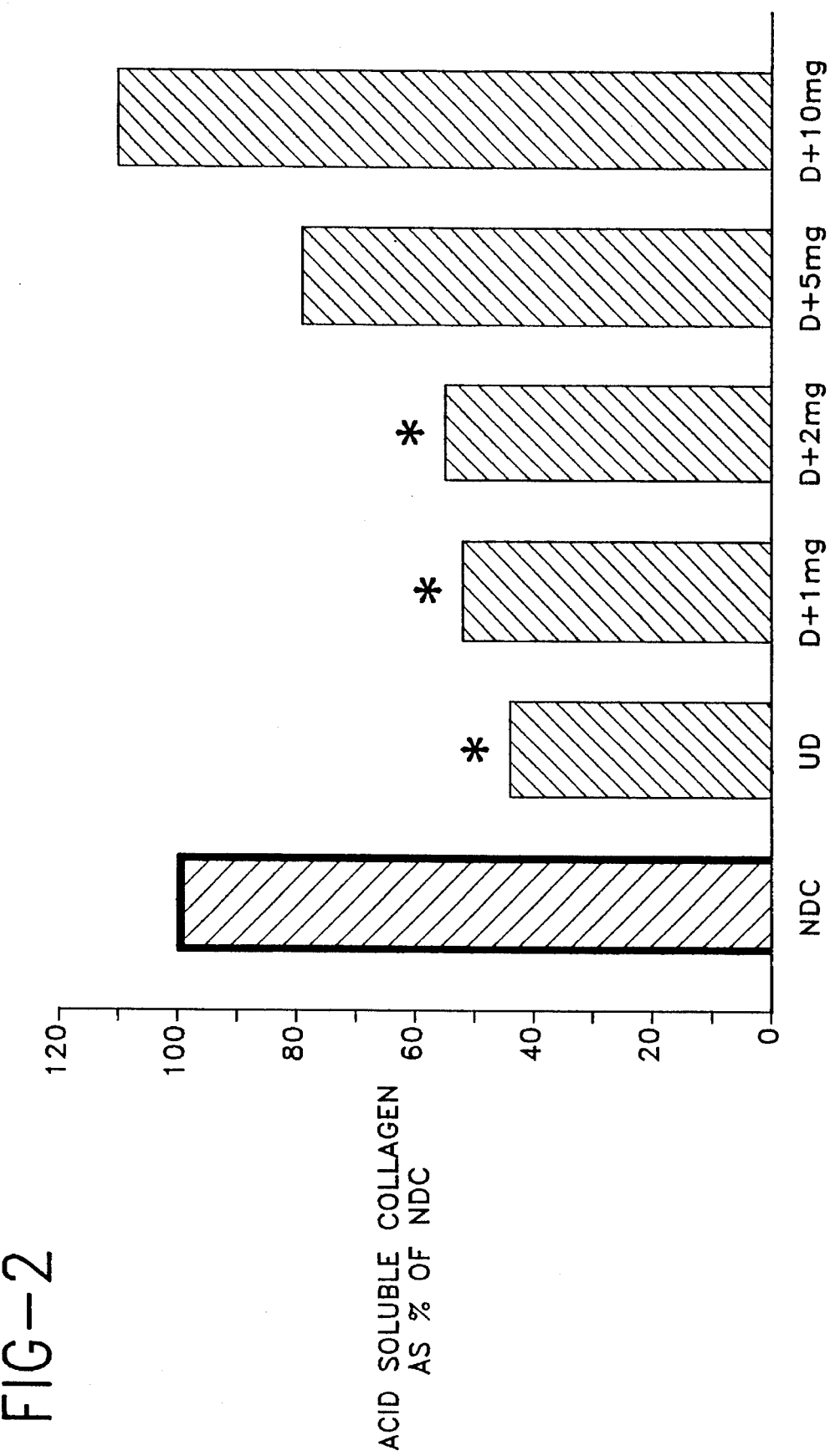
FIG. 2 is a graphic representation of the effect of CMT-1 (4-dedimethylaminotetracycline) therapy on the acid-soluble fraction of collagen in skin of diabetic rats. Note: the solubility of collagen in dilute acid (4° C.) was normalized to 100% for the non-diabetic control (NDC) rats and the data for the untreated diabetics (UD) and CMT-1 (4-dedimethylaminotetracycline) treated diabetics (D+mgs CMT-1) is expressed relative to the NDC values. * Indicates that value is significantly different from NDC ($p < 0.01$).
Figure 3:
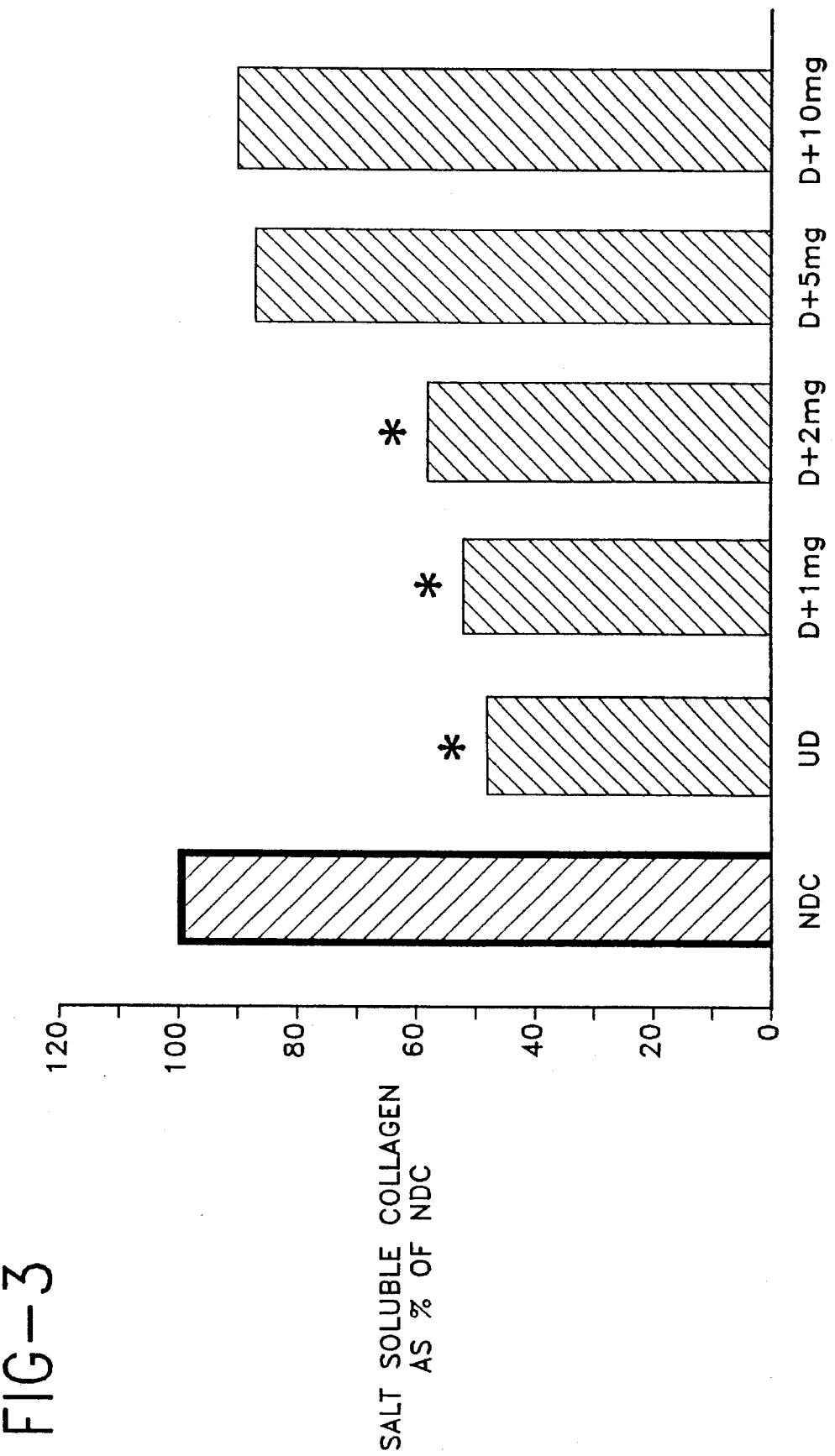
FIG. 3 is a graphic representation of the effect of CMT-1(4-dedimethylaminotetracycline) therapy on the salt-soluble fraction of collagen in skin of diabetic rats. Note: the solubility of collagen in neutral salt (4° C.) was normalized to 100% for the non-diabetic control (NDC) rats and the data for the untreated diabetics (UD) and CMT-1(4-dedimethylaminotetracycline) treated diabetics (D+mgs CMT-1) is expressed relative to the NDC values. *Indicates that value is significantly different from NDC ($p < 0.01$).

The data presented in FIGS. 2 and 3 shows the effect of diabetes and increasing oral doses of CMT-1 on the solubility of skin collagen in cold (4° C.) dilute acid and neutral salt solutions, respectively. As expected, the bulk of the collagen in the tissue (92%–96%) was insoluble in these solutions for both the NDC and diabetic rats (data not shown). Inducing diabetes reduced the solubility of skin collagen in neutral salt and dilute acid solutions by 52% and 56%, respectively ($p<0.01$). Note that the collagen solubility data was "normalized" to 100% for the salt-soluble and acid-soluble fractions in the skin of the non-diabetic control rats. Increasing the oral doses of CMT-1 administered to the diabetics progressively increased the abnormally low collagen solubility in neutral salt solutions by 10% (for the 1 mg CMT/day dose) up to 91% (for the 10 mg/day dose), and increased the low collagen solubility in dilute acid solutions by 18% (1 mg/day dose) up to 174% (10 mg/day dose). However, only the highest oral doses of CMT-1 administered to the diabetics, 5 and 10 mg/day, resulted in collagen solubility values that were similar to the normal values observed in the non-diabetic control rats (FIGS. 2 and 3).

CMT-1 therapy "normalized" the quality of collagen in the skin of diabetic animals by inhibiting the excess crosslinking which characterizes collagen in diabetic connective tissues.

As shown in Table II, a similar effect was seen when the diabetic rats were orally administered a commercially-available antimicrobial tetracycline, called minocycline (CMT-1, 4-dedimethylaminotetracycline is an analog of tetracycline which has lost its antimicrobial efficacy). As described above, the bulk of the collagen in the skin of the normal rats was insoluble in neutral salt and dilute acid Solutions (4° C.); only 5.8% and 10.7% of the collagen in the skin could be solubilized in 1M NaCl and 3% acetic acid, respectively. When the rats were made diabetic, collagen solubility was reduced, particularly in the dilute acid solutions ($p<0.05$) and the relative amount of insoluble collagen in skin was increased from a normal level of 83.5% to an abnormally high level of 88.8% in the diabetics ($p<0.05$). However, when the diabetics were treated with minocycline, the collagen solubility was returned to normal levels.

TABLE II

The Solubility of Skin Collagen in Neutral Salt and Dilute Acid Solutions (4° C.) in Diabetic Rats: Effect of Oral Administration of Minocycline (Mino) ☉

| Experimental Groups | Collagen Fractions (%) | | |
|---|---|---|---|
| | Salt-Soluble | Acid-Soluble | Insoluble |
| NDC | 5.8 ± 0.3 | 10.7 ± 1.9 | 83.5 ± 1.6 |
| UD | 4.5 ± 0.6 | 6.7 ± 0.2* | 88.8 ± 0.5* |
| D + 20 mg Mino/day | 5.8 ± 1.3 | 12.2 ± 1.9 | 82.0 ± 3.2 |

☉ Each value represents the mean of 3 rats per group ± S.E.M.
*Significantly different from other 2 groups ($p < 0.05$).

EXAMPLE II

Three groups of rats were established: a non-diabetic control group, an untreated streptozotocin-diabetic group and a streptozotocin-diabetic group treated orally with 2 mg doxycycline/rat/day over the 14-week time period. At the end of the 14 weeks, blood samples were collected from each rat arid the serum was measured for glycosylated protein using an assay which is based on the ability of glucose to non-enzymatically bind to proteins by a ketoamine crosslink to form fructosamine. During the assay, the glucose bound to the protein through a ketoamine chemical bond reduces a tetrazolium dye under alkaline conditions producing a color change which is measured spectrophotometrically. Armbruster, *Clin. Chem.*, 33: 2153–2163 (1987). A fructosamine assay kit is available from Isolab Inc., Akron, Ohio 44321.

In particular, the serum samples were centrifuged to remove lipids. The clarified serum samples were treated with a reagent to remove ascorbic acid and other interfering substances. The treated Serum samples were then incubated for a fixed period of time, with the fructosamine-bicarbonate reagent (tetrazolium salt), and absorbance was measured at a wavelength of 500 nm in a spectrophotometer. The data was analyzed statistically.

RESULTS

As seen in Table III, chronic diabetes (14-weeks duration) and chronic hyperglycemia significantly ($p<0.01$) increased the fructosamine level in serum proteins. These results provide evidence of non-enzymatic glycosylation, a reaction which is widely believed to be a major cause of many medical complications of long-term diabetes including pathologically excessive collagen crosslinking. Table III further shows that when the diabetics were treated on a daily basis with doxycycline, the fructosamine levels in the serum proteins of the diabetics were significantly ($p<0.05$) reduced. These results indicaite that administration of a tetracycline (e.g. doxycycline) inhibits non-enzymatic glycosylation of proteins during diabetes mellitus. However, this treatment does not reduce the severity of hyperglycemia in diabetic rats. Golub et al., *Res. Commun. Chem. Pathol. Pharmacol.*, 68:27–40 (1990).

TABLE III

| Experimental Groups of rats | Serum Fructosamine Concentration (mean ± standard error) |
|---|---|
| Non-diabetic Controls | 1.33 ± 0.05 |
| Untreated Diabetics | 3.82 ± 0.17 |

TABLE III-continued

| Experimental Groups of rats | Serum Fructosamine Concentration (mean ± standard error) |
| --- | --- |
| Doxycycline-treated Diabetics | 3.23 ± 0.20 |

EXAMPLE III

Example III was carried out to determine the effect of tetracycline therapy on proteinuria, a parameter of renal damage, in diabetic rats.

Streptozotocin-diabetic rats were treated by the daily oral administration of 20 mg minocycline/rat/day over a 4-week period. At the end of the protocol, 24-hour urines were collected to measure protein excretion.

RESULTS

Figure 4:
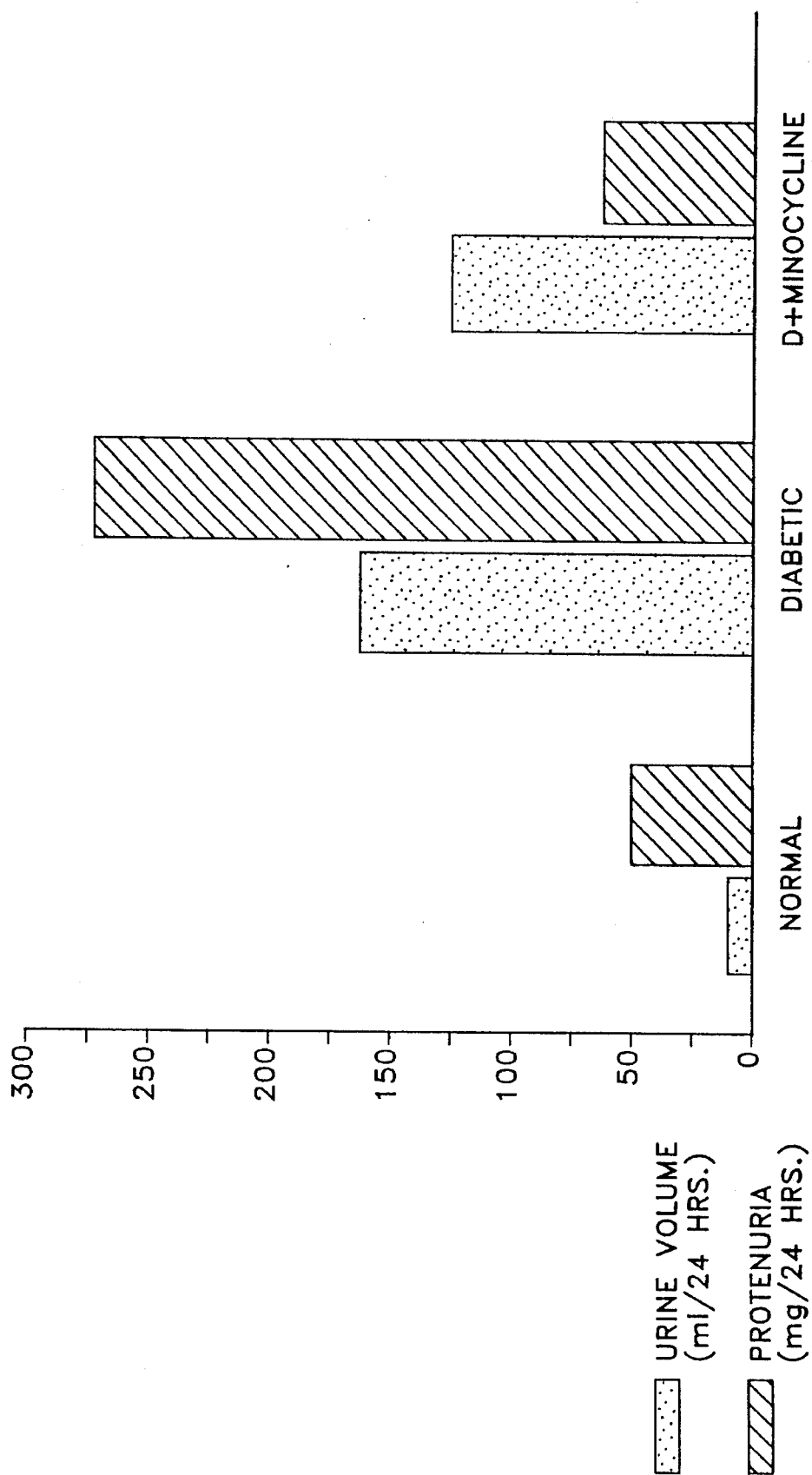
FIG. 4 is a graphic representation of the effect of minocycline therapy on urine excretion and proteinuria in diabetic rats.

As shown in FIG. 4, the excretion of protein in the urine increased from 48 mg/24 hr in the normal (non-diabetic) rats to 280 mg/24 hr in the untreated diabetics, a 483% increase. Surprisingly, the daily oral administration of minocycline completely prevented the development of proteinuria in the diabetic rats. FIG. 4 shows that the minocycline-treatment resulted in urine protein excretion of 52 mg/24 hr. Neither treatment with minocycline nor CMT-1 reduced the other signs of diabetes including hyperglycemia, glucosuria and polyuria. The prevention of proteinuria further demonstrates the ability of the tetracyclines of the present invention to inhibit excessive collagen glycosylation and the resulting collagen crosslinking. Recent experiments using a chemically modified non-antimicrobial tetracycline (CMT-1; 4-dedimethylaminotetracycline) also found a reduction in proteinuria in diabetic rats (data not shown). Golub et al., *Matrix*, suppl 31:315–316 (1992).

EXAMPLE IV

The effects of Doxycycline and CMT-1 (4-dedimethylaminotetracycline) on glycosylation of proteins during diabetes was measured. Sixteen adult male sprague-Dawley rats, each weighing approximately 350 grams, were divided into four groups 0f four animals per group. Diabetes was induced by I.V. administration of streptozotocin in all rats, except the non-diabetic control group (4 rats). All diabetic= rats were given 5mg of the following treatments daily by oral gavage for a period of twenty-one (21) days. Group I: CMT-1 (4-dedimethylaminotetracycline), Group II: Doxycycline (an antimicrobial tetracycline), Group III: non-diabetic control rats administered vehicle alone (2% carboxymethyl-cellulose and Group IV: untreated diabetic control rats administered vehicle alone (2% carboxymethylcellulose).

Following general anesthesia by halothane inhalation, blood samples were collected by cardiac puncture. Blood samples were analyzed for serum glucose and glycosylated serum protein levels. Glycosylated serum protein levels were measured using the Glyco-Probe™ GSP kit from Isolab, Inc., Akron, Ohio.

In addition, the entire skin was dissected from each rat. Samples containing 100mg of each skin were suspended in a Tris-HCl buffer containing 5mM $CaCl_2$ and chromatographically-purified bacterial collagenase and incubated at 37° C. for 4 hours. Following incubation all samples were centrifugated at 35,000×G and the supernatants containing the skin collagen fragments were collected. The skin digest supernatants were analyzed for (1) carbohydrate-attached-to-collagen by the anthrone method, as described by Halhoul and Kleinberg (1992) *Anal. Biochem.* 50: 337–343 and (2) total protein using the BioRad Assay, BioRad Chemical Division, Richmond, Calif.

RESULTS

Figure 5:
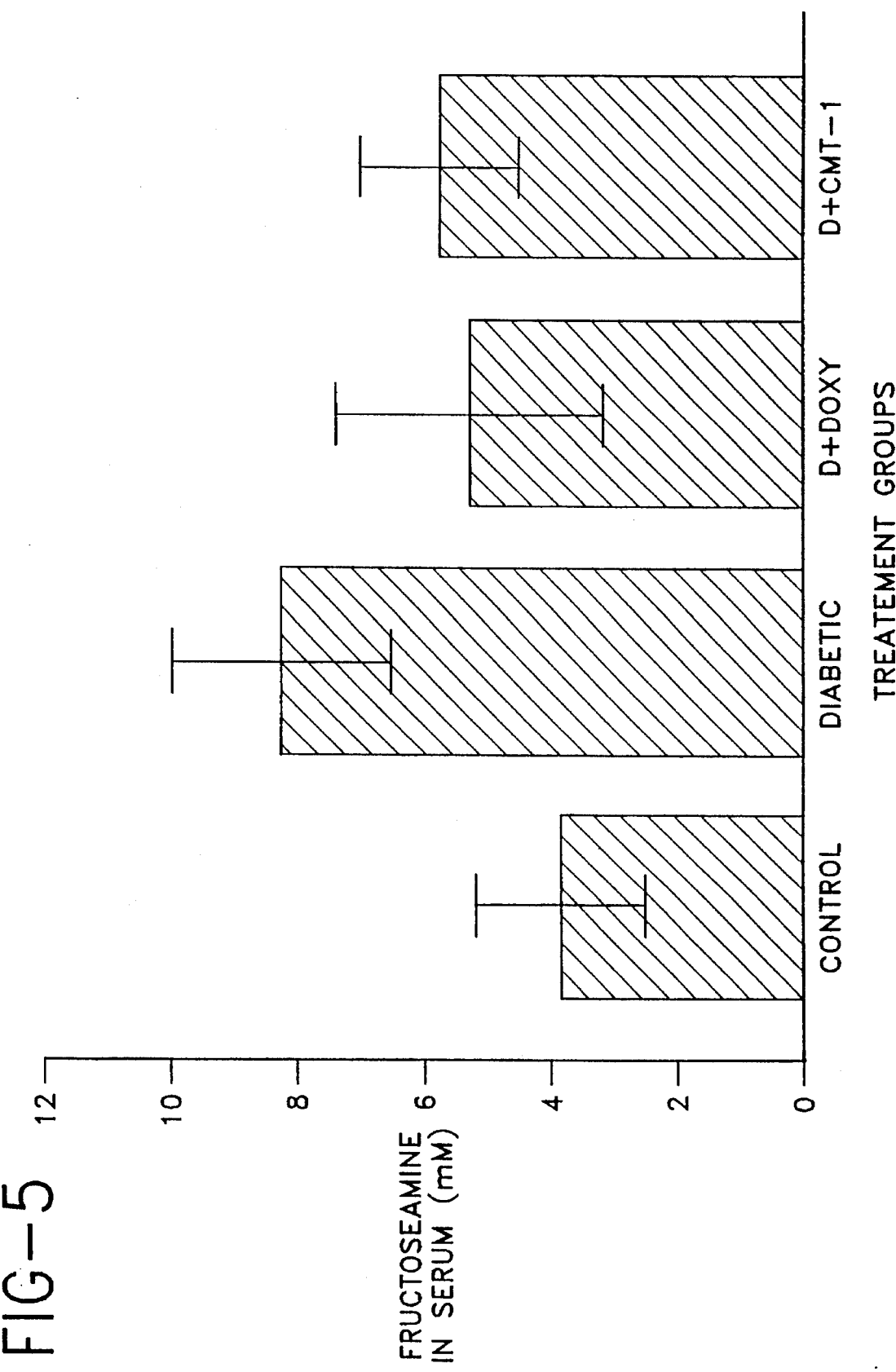
FIG. 5 is a graphic representation of the effect of doxycycline and CMT-1 (4-dedimethylaminotetracycline) on glycosylated serum proteins in streptozotocin-diabetic rats. (Control vs. Diabetic $p<0.01$, Diabetic vs. Diabetic treated with Doxycycline $p<0.05$, Diabetic vs. Diabetic treated with CMT-1 (4-dedimethyiaminotetracycline) $p<0.05$).
Figure 6:
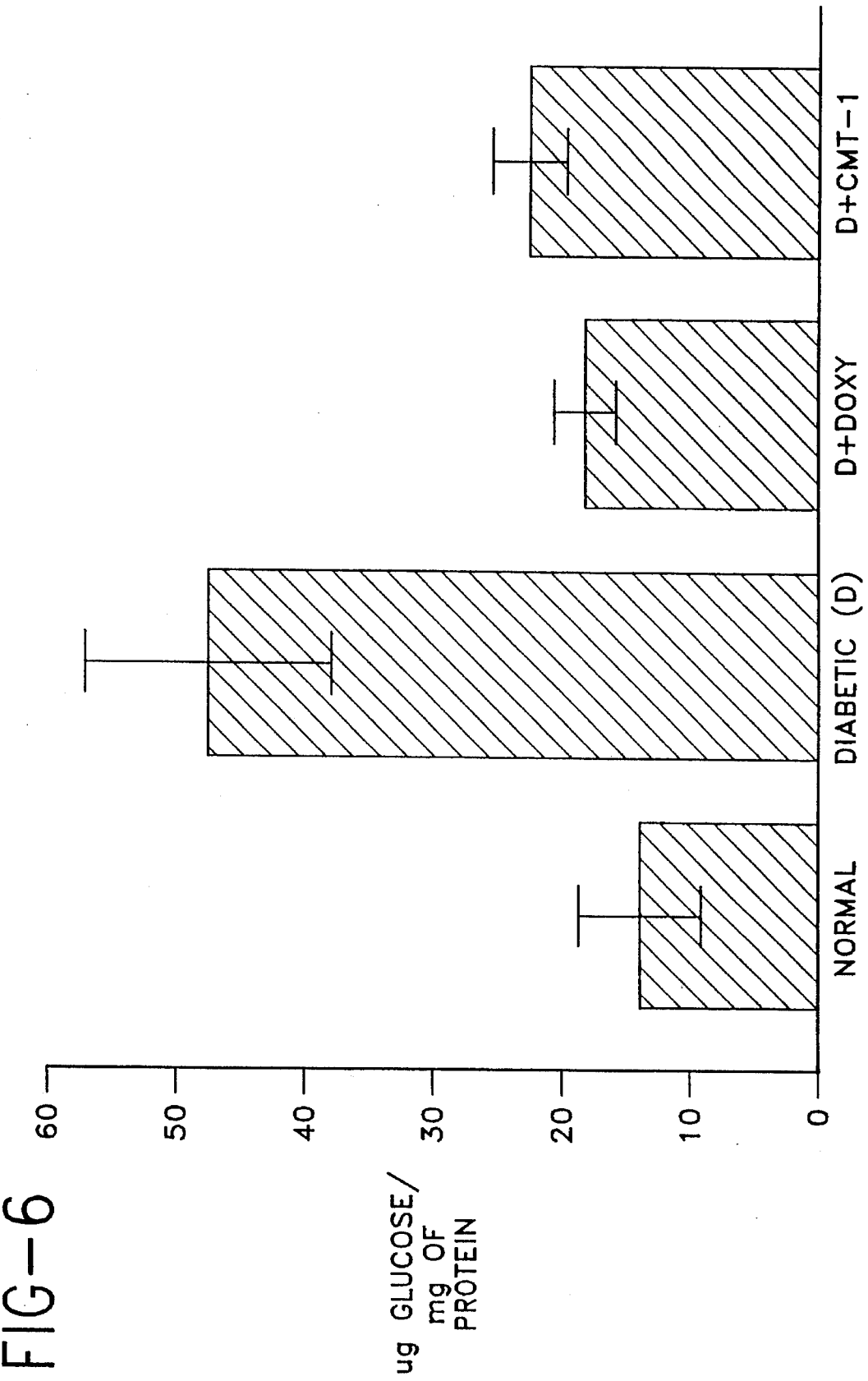
FIG. 6 is a graphic representation of the effect of doxycycline and CMT-1 (4-dedimethylaminotetracycline) on glycosylation of skin collagen in streptozotocin-diabetic rats.

As shown in FIGS. 5 and 6, diabetics have significantly increased (1) fructosamine attached to serum protein ($p<0.01$) (FIG. 5), and (2) the data is consistent with increased glycosylation of skin collagen ($p<0.01$) (FIG. 6). Treatment of diabetic rats by the oral administration of either doxycycline or CMT-1 (4-dedimethylaminotetracycline) returned both of these parameters of abnormal glycosylation to essentially normal levels. In addition, the effects of both drugs on glycosylated serum protein and on glycosylation of skin collagen were statistically significant ($p<0.05$).

EXAMPLE V

The effects of several CMTs and Doxycycline, an antimicrobial tetracycline, on non-enzymatic glycosylation, an extracellular pathway widely believed to be responsible for many (sometimes life-threatening) complications of diabetes mellitus was measured. CMT-5 (tetracycline pyrazole), which is the only CMT reported to have lost its anticollagenase properties, as assessed in vitro (Golub, et al., 1991) and in vivo, was used as a control therapy in this model. Fifty-two adult male Sprague-Dawley rats were divided into eight groups, each consisting of 5–7 animals. Diabetes was induced by I.V. administration of streptozotocin in all rats, except the non-diabetic control group (7 rats). All diabetic rats were given 5mg of the following treatments daily by oral gavage for a period of 21 days, Group I: CMT-3 (6-demethyl-6-deoxy-4-dedimethylaminotetracycline), Group II: CMT-4 (7-chloro-4-dedimethylaminotetracycline), Group III: CMT-5 (tetracycline pyrazole), Group IV: CMT-7 (12a-deoxy- 4-deoxy-4-dedimethylaminotetracycline), Group V: CMT-8 (6α-deoxy-5-hydroxy-4-dedimethylaminodoxycycline) Group VI: Doxycycline, Group VII: non-diabetic control administered vehicle alone (2% carboxymethylcellulose) and Group VIII: untreated diabetic control administered vehicle alone (2% carboxymethylcellulose). In addition, two of the diabetic rats were treated with CMT-1 (4-dedimethylaminotetracycline) over the 21-day time period. All animals were weighed weekly. Following general anesthesia by halothane inhalation, blood samples were collected by cardiac puncture. Blood samples were analyzed for serum glucose and glycosylated serum protein (GSP) levels. As previously mentioned, glycosylated serum protein levels were measured using the Isolab Glyco-PROBE™ GSP (glycosylated serum protein) assay kit. Following sacrifice the skins were dissected and one-half of each skin was minced and assayed for interstitial MMP activity, i.e., collagenase and gelatinase. The other half of the skin from each rat was frozen at −80° C. until part of it was processed and analyzed for glycosylation of skin collagen.

In particular, all dissection and extraction procedures were carried out at 4° C. unless otherwise indicated. For MMP analysis, the tissues were minced, weighed, extracted, and the extracts partially purified by ammonium sulfate precipitation using techniques described previously (Ramamurthy and Golub, *J. Periodontal Res.* 17, 455, (1983)). The extracts of the diseased tissue were then concentrated 5-fold and aliquots were incubated (a) with [$^3$H-methyl] gelatin (denatured type I rat skin collagen) at 37° C. for 4 hours to measure gelatinase activity. The undigested gelatin was precipitated with trichloroacetic acid, and after centrifugation, aliquots of the degradation products in the supernatants were measured in a liquid scintillation spectrometer (in addition to this lysis assay, the different molecular forms of gelatinase were assessed by zymography); (b) with [$^3$H-methyl] collagen for 18 hours at 27° C. and the collagen degradation fragments in the supernatants were analyzed with a liquid scintillation spectrometer to measure collagenase activity. In addition, the radiolabeled collagen components ($\alpha$ chains) and degradation fragments ($\alpha^A$) were assessed by a combination of SDS-polyacrylamide gel electrophoresis and fluorography as described previously (Golub et al. *J. Periodontal Res.* 20, 12 (1985).

For analysis of glycosylation of collagen, the other half of the skin from each of the rats was treated as follows: the hair and the epidermal layer were removed by scraping. The subcutaneous muscle layer was removed leaving essentially the dermis. The dermis (skin connective tissue) samples were minced, then homogenized in phosphate buffered saline (4° C.). Following centrifugation (at 9000 rpm, 4° C., 30 min.) of the homogenates, the supernatants were discarded. The pellets were repeatedly washed, then resuspended and extracted at 4° C. overnight in chloroform/methanol to remove lipids. The de-lipidized tissue samples were then washed in 100% methanol, then in 50% methanol. Following the methanol washes, the samples were washed with HEPES buffer (pH 7.4). The skin connective tissue samples (100 mg of each sample) were incubated at 37° C. (24 hours) with chromatographically-purified bacterial collagenase. After 24 hours the reaction mixture was centrifuged at 7000 rpm, room temperature for 30 minutes. Following centrifugation, the supernatants containing the digested collagen were collected. Aliquots of the supernatants were analyzed for glycosylated collagen using a modification of the Isolab Glyco-PROBE™ GSP assay kit. The assay is designed to measure glucose bound to protein which was then converted by Amadori rearrangement to fructosamine. For purposes of the present invention, the sample total protein was increased to compensate for low levels of glycosylated collagen compared to glycosylated serum proteins.

RESULTS

Body weight gain was seen in all groups except for the CMT-5 (tetracycline pyrazole) group, which maintained its body weight, and the untreated diabetic group which lost weight. The blood glucose concentration was significantly higher in diabetic groups than in the normal control group. No difference was seen in blood glucose concentration in untreated and treated diabetics. As shown in FIG. 7, the GSP levels were substantially lower in all treatment groups, including CMT-5 (tetracycline pyrazole) ($p<0.005$), in comparison to the elevated levels seen in the untreated diabetics, and approached the level of GSP found in normal controls. As shown in TABLE IV, the pathologically-excessive glycosylation of skin collagen in the diabetics was also reduced to near normal levels by a number of these drugs, when the data is expressed per mg protein (See TABLE IV) or expressed per mg skin collagen (as determined by hydroxyproline analysis of skin hydrolysate, data not shown).

The therapeutic effect of various tetracycline derivatives on collagenase and gelatinase activity in the skin of diabetic rats is shown in FIGS. 8 and 9, respectively. As shown in the Figures, elevated gelatinase and collagenase activity in the skins of the diabetic animals was normalized by all treatment groups ($p<0.001$) with the exception of CMT 5 (tetracycline pyrazole) as determined by lysis assays, zymography (data not shown) and fluorography (data not shown). These results indicate that the pathologic levels of MMPs can be normalized in vivo by treatment with doxycycline and various CMTs. In addition, it can be seen, based on the CMT-5 (tetracycline pyrazole) data, that extracellular glycosylation of proteins in the diabetic was inhibited by tetracycline and their analogs by a completely separate mechanism from the mechanism by which these drugs inhibit collagenase and gelatinase.

TABLE IV

Glycosylation of Diabetic Rat Skin Collagen: Inhibition by Different CMTs

| Treatment group | mM Fructosamine/mg protein (Mean ± SE) | Reduction of glycosylation in treated diabetics (%) |
| --- | --- | --- |
| Non-Diabetic Control (NDC) | 0.027 ± 0.018*** | — |
| Diabetic Untreated Control (DUC) | 0.377 ± 0.082 | — |
| D + Doxycycline | 0.244 ± 0.050# | 35.3 |
| D + CMT-1 | 0.123 ± 0.011* | 67.4 |
| D + CMT-3 | 0.186 ± 0.048* | 50.7 |
| D + CMT-4 | 0.236 ± 0.026# | 37.4 |
| D + CMT-5 | 0.121 ± 0.050** | 69.9 |
| D + CMT-7 | 0.141 ± 0.086* | 62.6 |
| D + CMT-8 | 0.118 ± 0.090**a | 68.7 |

All significance are based on two tailed t test
\* = p < 0.05 from Diabetic Untreated Control
\*\* = p < 0.025 from Diabetic Untreated Control
\*\*\* = p < 0.005 from Diabetic Untreated Control
\# = not significantly different from Diabetic Untreated Control
a = not significantly different from Non-Diabetic Control These experimental results, using both antimicrobial and non-antimicrobial forms of tetracycline, demonstrate a powerful new pharmacological approach for preventing apparent accelerated aging or excessive crosslinking of collagen, an abnormality widely believed to be responsible for many of the serious complications of diabetes.

Thus, while there has been described what are presently believed to be the preferred embodiments of the invention, those skilled in the art will understand that other and further modifications can be made without departing from the spirit of the invention. It is intended that the present invention includes all such modifications as come within the true scope of the invention as set forth in the claims.

What is claimed:

1. A method of treating a mammal suffering from conditions associated with a pathologically excessive amount of protein glycosylation comprising administering to the mammal an effective amount of a tetracycline sufficient to inhibit said pathologically excessive amount of protein glycosylation.

2. The method of claim 1, wherein a protein which is subject to said pathologically excessive amount of protein glycosylation is a somatic protein with exposed amino groups.

3. The method of claim 2, wherein said somatic protein with exposed amino groups is selected from the group consisting of collagen, laminin, albumin, lens crystallins and fibrin.

4. The method of claim 2, where in said protein is associated with pathological conditions including diabetes mellitus, scleroderma and progeria.

5. The method of claim 3, wherein said protein is collagen and said pathologically excessive amount of collagen glycosylation results in a pathologically excessive amount of collagen crosslinking.

6. The method of claim 5, wherein said pathologically excessive amount of collagen crosslinking is associated with conditions including diabetes mellitus, scleroderma and progeria.

7. The method according to claim 1, wherein the tetracycline is a dedimethylaminotetracycline.

8. The method according to claim 7, wherein the dedimethylaminotetracycline is selected from the group consisting of 4-dedimethylaminotetracycline, 4-dedimethylamino-5-oxytetracycline, 4-dedimethylamino-7chlorotetracycline, 4-hydroxy-4-dedimethylaminotetracycline, 5a,6-anhydro-4-hydroxy-4-dedimethylaminotetracycline, 6α-deoxy-5-hydroxy-4-dedimethylaminotetracycline, 6-demethyl-6-deoxy-4-dedimethylaminotetracycline, 4-dedimethylamino-12a-deoxytetracycline, 12a-deoxy-4-deoxy-4-dedimethylaminotetracycline, 12a, 4a-anhydro-4-dedimethylaminotetracycline, 7-dimethylamino-6-demethyl-6-deoxy-4-dedimethylaminotetracycline and 4-dedimethylamino-11-hydroxy-12a-deoxytetracycline.

9. The method according to claim 1, wherein the tetracycline is selected from the group consisting of 6a-benzylthiomethylenetetracycline, tetracyclinonitrile, the mono-N-alkylated amide of tetracycline, 6-fluoro-6-demethyltetracycline, 11a-chlorotetracycline, tetracycline pyrazole, 6α-deoxy-5-hydroxy-4-dedimethylaminodoxycycline and 12a-deoxytetracycline and its derivatives.

10. The method according to claim 1, wherein the tetracycline is administered in an amount of from about 0.1 mg/kg per day to about 50.0 mg/kg per day.

11. The method according to claim 10, wherein the tetracycline is administered in an amount of from about 0.3 mg/kg per day to about 15.0 mg/kg per day.

* * * * *